US011666396B2

United States Patent
Kapadia et al.

(10) Patent No.: US 11,666,396 B2
(45) Date of Patent: *Jun. 6, 2023

(54) MOUNTING DEVICE FOR SURGICAL SYSTEMS AND METHOD OF USE

(71) Applicant: Covidien LP, Mansfield, MA (US)

(72) Inventors: Jaimeen Kapadia, Cambridge, MA (US); Josiah Rosmarin, Sebring, FL (US)

(73) Assignee: Covidien LP, Mansfield, MA (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/062,683

(22) Filed: Oct. 5, 2020

(65) Prior Publication Data

US 2021/0015567 A1  Jan. 21, 2021

Related U.S. Application Data

(63) Continuation of application No. 15/580,366, filed as application No. PCT/US2016/035980 on Jun. 6, 2016, now Pat. No. 10,799,304.
(Continued)

(51) Int. Cl.
*A61B 34/30* (2016.01)
*A61B 34/35* (2016.01)
(Continued)

(52) U.S. Cl.
CPC .............. *A61B 34/30* (2016.02); *A61B 17/00* (2013.01); *A61B 34/35* (2016.02);
(Continued)

(58) Field of Classification Search
CPC .. A61B 2017/00477; A61B 2017/2926; A61B 2034/305
See application file for complete search history.

(56) References Cited

U.S. PATENT DOCUMENTS 2,722,727 A   11/1955 Scheifele
3,146,846 A    9/1964 Gutshall
(Continued)

FOREIGN PATENT DOCUMENTS

DE    102008020489 A1   10/2009
DE    102013002813 A1    8/2014
(Continued)

OTHER PUBLICATIONS

Indian Office Action dated Jun. 24, 2021 corresponding to counterpart Patent Application IN 201717045720.
(Continued)

*Primary Examiner* — Alexander J Orkin
(74) *Attorney, Agent, or Firm* — Carter, DeLuca & Farrell LLP

(57) ABSTRACT

A surgical mounting device may detachably couple to a patient access device to maintain alignment between a surgical instrument and the access device as instruments are interchangeably inserted and removed from the access device. The mounting device may include arms that pivot between a closed configuration in which the arms grip the access device inserted therebetween and an open configuration in which arm are spaced further apart from each other than in the closed configuration. A drive member may transition the arms to the closed configuration when the patient access device is inserted between the arms in the open configuration and pressed against the drive member.

18 Claims, 11 Drawing Sheets

Related U.S. Application Data

(60) Provisional application No. 62/172,396, filed on Jun. 8, 2015.

(51) Int. Cl.
*A61B 17/00* (2006.01)
*A61B 17/34* (2006.01)

(52) U.S. Cl.
CPC .............. *A61B 2017/00477* (2013.01); *A61B 2017/00526* (2013.01); *A61B 2017/3409* (2013.01); *A61B 2034/305* (2016.02)

(56) References Cited

U.S. PATENT DOCUMENTS

| | | | |
|---|---|---|---|
| 4,845,834 | A | 7/1989 | Watson |
| 4,878,705 | A | 11/1989 | Arnquist |
| 5,380,338 | A | 1/1995 | Christian |
| 5,779,623 | A | 7/1998 | Bonnell |
| 5,845,377 | A | 12/1998 | Bibeault |
| 6,451,027 | B1 | 9/2002 | Cooper et al. |
| 8,182,469 | B2 | 5/2012 | Anderson et al. |
| 8,828,023 | B2 | 9/2014 | Neff et al. |
| 10,004,563 | B2 | 6/2018 | Gombert et al. |
| 10,799,304 | B2 | 10/2020 | Kapadia et al. |
| 2003/0190184 | A1 | 10/2003 | O'Brien |
| 2007/0194173 | A1 | 8/2007 | Paasche |
| 2010/0207385 | A1 | 8/2010 | Nishimura |
| 2010/0286669 | A1 | 11/2010 | Greer et al. |
| 2012/0116416 | A1 | 5/2012 | Neff et al. |
| 2012/0126079 | A1 | 5/2012 | Russell |
| 2013/0167470 | A1 | 7/2013 | Montgomery |
| 2013/0182381 | A1 | 7/2013 | Gray |
| 2014/0180308 | A1 | 6/2014 | von Grunberg |
| 2014/0299313 | A1 | 10/2014 | Messmer |
| 2015/0374445 | A1 | 12/2015 | Gombert et al. |

FOREIGN PATENT DOCUMENTS

| | | |
|---|---|---|
| JP | 55157493 | 12/1980 |
| JP | 01210294 | 8/1989 |
| JP | 2010531672 A | 9/2010 |
| JP | 2014508546 A | 4/2014 |
| WO | 2014127984 A1 | 8/2014 |

OTHER PUBLICATIONS

ISR Written Opinion of PCT/US2016/035980 dated Sep. 12, 2016.
Extended European Search Report corresponding to counterpart Patent Appln. EP 16808079.4 dated Jan. 17, 2019.
Australian Examination Report No. 1 dated Feb. 28, 2020 corresponding to counterpart Patent Application AU 2016274414.
Chinese First Office Action dated Dec. 23, 2019 corresponding to counterpart Patent Application CN 201680033339.9.
Japanese Office Action dated Apr. 1, 2020 corresponding to counterpart Patent Application JP 2017-563186.
Chinese Second Office Action dated Aug. 14, 2020 corresponding to counterpart Patent Application CN 201680033339.9.
Australian Examination Report No. 1 dated Feb. 5, 2021 corresponding to counterpart Patent Application AU 2020203791.
Japanese Notice of Allowance corresponding to counterpart Patent Application No. JP 2020-132804 dated Nov. 22, 2021; and machine generated English Translation.
European Office Action dated Oct. 12, 2021 corresponding to counterpart Patent Application EP 16 808 079.4.
Canadian Office Action dated Nov. 22, 2022, issued in corresponding Canadian Appln. No. 2,987,061, 7 pages.

MOUNTING DEVICE FOR SURGICAL SYSTEMS AND METHOD OF USE

CROSS-REFERENCE TO RELATED APPLICATIONS

The present application claims the benefit of, priority to, and is a Continuation application of U.S. patent application Ser. No. 15/580,366, filed on Dec. 7, 2017, now U.S. Pat. No. 10,799,304, which is a U.S. National Stage Application filed under 35 U.S.C. § 371(a) of International Patent Application No. PCT/US2016/035980, filed on Jun. 6, 2016, which claims the benefit of and priority to U.S. Provisional Patent Application No. 62/172,396, filed on Jun. 8, 2015, the entire contents of each of which being hereby incorporated by reference in its entirety.

BACKGROUND

Technical Field

Robotic surgical systems used in minimally invasive medical procedures included a console supporting a robot arm which further supported patient access devices, for example, a trocar, surgical port, or the like, through which a surgical instrument having an end effector (e.g., forceps, staplers, grasping tools, etc.) were passed through for use during the medical procedure. The robot arm coupled to the access device and the surgical instrument and moved the access device as the surgical instrument was moved during the procedure. A robot arm included an instrument drive unit that operatively connected to the surgical instrument.

Prior to or during use of the robotic system, access devices were connected to each robot arm to maintain alignment of the access device with the robot arm after the surgical instruments were removed from the access device and/or robot arm. Certain connecting features of the access devices had to be matingly engaged to corresponding connecting features of the robotic arm to complete the connection. The connection and removal of these access devices required precise alignment and was time consuming.

There is a need for more efficient connectivity between access devices and robot arms.

SUMMARY

Surgical mounting devices may include a first arm and a second arm pivotable between a closed configuration in which the first and second arms grip a patient access device inserted therebetween and an open configuration in which a portion of the first and second arms are spaced further apart from each other than in the closed configuration. Surgical mounting devices may also include a drive member coupled between the first and second arms, the drive member driving the arms to the closed configuration when the patient access device is inserted between the arms in the open configuration and pressed against the drive member. These features may enabling access devices to be quickly attached and detached to the surgical mounting device and/or surgical robotic arm when the surgical mounting device is part of the robotic arm.

The surgical mounting device may also include a surgical robotic arm having an end portion positioned near a surgical access site on the patient. The first and second arms may protrude from the end portion of the surgical robotic arm.

A release mechanism that may be part of the surgical mounting device may bias the first and the second arms toward the open configuration when actuated. The release mechanism may define an actuation pivot point, such that the release mechanism is pivotable between a non-actuated position and an actuated position. The release mechanism may include a hooked end cooperatively engaging with a surface of the drive member in an actuated position. The release mechanism may include a chamfered profile engaging with a proximal surface of the drive member in an actuated position. The release mechanism may be biased towards a non-actuated position.

The surgical mounting device may also include two release mechanisms disposed on opposing sides of the housing. In some instances, actuation of both these release mechanisms may bias the first and the second arms toward the open configuration. In some instances, actuation of either of these release mechanisms may bias the first and the second arms toward the open configuration.

The first and second arms may have an arcuate surface corresponding to an arcuate surface of the patient access device gripped by the arms.

A surgical mounting device may selectively grip a patient access device therein. The surgical mounting device may include a housing, a clamping assembly supported in the housing and extending therefrom. The clamping assembly may include a plunger assembly supported on the housing and a drive member disposed in the housing coupled to a middle segment disposed distal to the housing. The drive member and middle segment may simultaneously translate between a proximal position and a distal position with respect to the housing.

A first and a second arm may be supported by the housing and include a proximal portion disposed in the housing and a distal portion extending therefrom. Each arm may be coupled at the proximal end to the drive member and pivotable with respect to the housing between an open position and a closed position. In the open position the first and second arms may be spaced apart relative to one another and in the closed position the first and second arms may be in an approximated position relative to one another.

The clamping assembly may be transitionable between an unlocked configuration and a locked configuration. In the unlocked configuration, the drive member and the middle segment may be in the distal position and the first and second arms may be in the open position. In the locked configuration, the drive member and middle segment may be in the proximal position and the first and second arms may be in the closed position.

The surgical mounting device and/or clamping assembly may include at least one release mechanism. The release mechanism may include a contact surface disposed in the housing and an articulation member in operative communication with the contact surface. A portion of the articulation member may be disposed externally from the housing, The release mechanism may be transitionable between an initial position and a release position, such that in the initial position the contact surface is spaced away from the drive member, and in the release position the contact surface is in abutment with the drive member. The release position may translate the drive member into the distal position, such that the clamping assembly is transitioned into the unlocked configuration. The release mechanism may include two release mechanisms disposed in opposite sides of the housing.

Each arm may further include an arcuate surface on the distal portion. The middle segment may further include an arcuate surface on a distally facing surface. The first arm, the second arm, and the middle segment may further include a protruding ridge disposed on each of the arcuate surfaces.

The clamping assembly may further include at least one biasing member coupled between the proximal end of each of the first and second arms. The biasing member may bias the first and second arms into the open position, and bias the drive member and middle segment coupled therewith into the distal position.

Each arm may further include a pivot point disposed distal to the proximal end, such that pivoting the arms from the open position to the closed position translates the drive member and middle segment coupled therewith from the distal position to the proximal position transitioning the clamping assembly into the locked configuration.

The middle segment may translate from the proximal position to the distal position, such that the drive member coupled therewith translates distally and the first and second arms pivot from the open position to the closed position transitioning the clamping assembly into the locked configuration.

The plunger assembly may include a biasing member disposed between the middle segment and the drive member, such that the middle segment is biased distally with respect to the drive member.

The release mechanism may include a biasing member such that the at least one release mechanism is biased into the initial condition.

An access device may be mounted to a surgical system via a surgical mounting device. Responsive to positioning the access device into abutment with a middle segment situated between a pair of arms extending distally from a housing of the surgical mounting device on opposing sides of the middle segment, a driving mechanism slidably disposed in the housing and operably coupled to the middle segment may be translated from a distal position to a proximal position.

Responsive to translating the driving mechanism, the pair of arms coupled at a proximal end to the drive mechanism may be pivoted from a spaced apart position relative to one another to an approximated position relative to one another.

The drive mechanism may be translated into the proximal position and the pair of arms may be pivoted into the approximated position responsive to depressing the middle segment with the access device.

The pair of arms may grip the access device responsive to pivoting the pair of arms while the access device is positioned therebetween.

In response to translating a release mechanism into a release position: a contact surface of the release mechanism may be abutted with the driving mechanism, the driving mechanism may be translated into the distal position, the middle segment may be translated into the distal position, and the pair of arms may be pivoted into the spaced apart configuration.

Surgical mounting devices may be affixed to a robot arm of a surgical robotic system and include a housing and a clamping assembly enabling access devices to be quickly attached and detached to the robot arm. The clamping assembly may be supported on the housing and includes a first arm, a second arm, and a plunger assembly. The first and second arms may extend distally from the housing and may be coupled at a proximal end to a drive member. Further, the first and second arms may be pivotable between an open configuration and a closed configuration. In the open configuration a distal portion of each of the first and second arms may be spaced apart from one another, and in the closed configuration the distal portions of each first and second arm may be approximated relative to one another.

The plunger assembly may be supported in the housing and include the drive member coupled to a middle segment. The drive member may be disposed in the housing and the middle segment may be disposed distal to the housing between the first and second arms. The drive member may be translatable between a proximal position and a distal position with respect to the housing. The clamping assembly may be translatable between an open configuration and a closed configuration. In the open configuration the first and second arms may be in the open configuration and the drive member, and middle segment coupled thereto, may be in the distal portion. In the closed configuration the first and second arms may be in the closed configuration and the drive member, and middle segment coupled thereto, may be in the proximal position.

In an embodiment, the surgical mounting device may include at least one release mechanism supported on the housing. The at least one release mechanism may include a contact surface disposed in the housing and coupled to an articulation member. A portion of the articulation member may extend externally of the housing. The at least one release mechanism may be translatable between an initial position and a release position. In the initial position, the contact surface may be spaced apart from the drive member, and in the release position, the contact surface may be in abutment with the drive member. In the release position the clamping assembly may be urged to transition into the open configuration.

The contact surface and the articulation member of the at least one release mechanism may be monolithically formed. The at least one release mechanism may define a pivot point, and may be pivotable between the initial position and the release position. The contact surface of the at least one release mechanism may define a hooked end, and the hooked end may cooperatively engage with a proximal surface of the drive member in the release position. The contact surface of the at least one release mechanism may define a chamfered profile, and the chamfered profile may cooperatively engage with a proximal surface of the drive member in the release position. The at least one release mechanism may be biased towards the initial position. The at least one release mechanism may include two release mechanisms disposed on opposing sides of the housing. Translation of the at least one release mechanism from the initial position to the release position may translate the drive member, and the middle segment coupled therewith, from the proximal position to the distal position.

The first and second arms may further include an arcuate surface disposed on an inner facing surface of the distal portion relative to one another, and the middle segment may further include an arcuate surface disposed on an outer facing surface with respect to the housing. The first and second arms, and the middle segment, may further include a protruding ridge disposed on the arcuate surface.

Each of the first and second arms may pivot about a point distal to the proximal end. As a result, as first and second arms pivot from the open configuration to the closed configuration, the drive member and the middle segment coupled therewith translate from the distal position to the proximal position. Thus, the clamping assembly transitions from the open configuration to the closed configuration.

The middle segment may be translatable from a distal position to a proximal position. As a result, the drive member coupled therewith translates simultaneously from the distal position to the proximal position, and the first and second arms pivot from the open configuration to the closed configuration. Thus, the clamping assembly transitions from the open configuration to the closed configuration.

The plunger assembly may include a spring disposed between the middle segment and the drive member. The spring may bias the middle segment distally with respect to the drive member.

The clamping assembly may include at least one spring coupled to the proximal ends of each of the first and second arms. The at least one spring may bias the first and second arms into the open configuration and the drive member, and middle segment coupled therewith, may be biased into the distal position.

DETAILED DESCRIPTION

Figure 1:
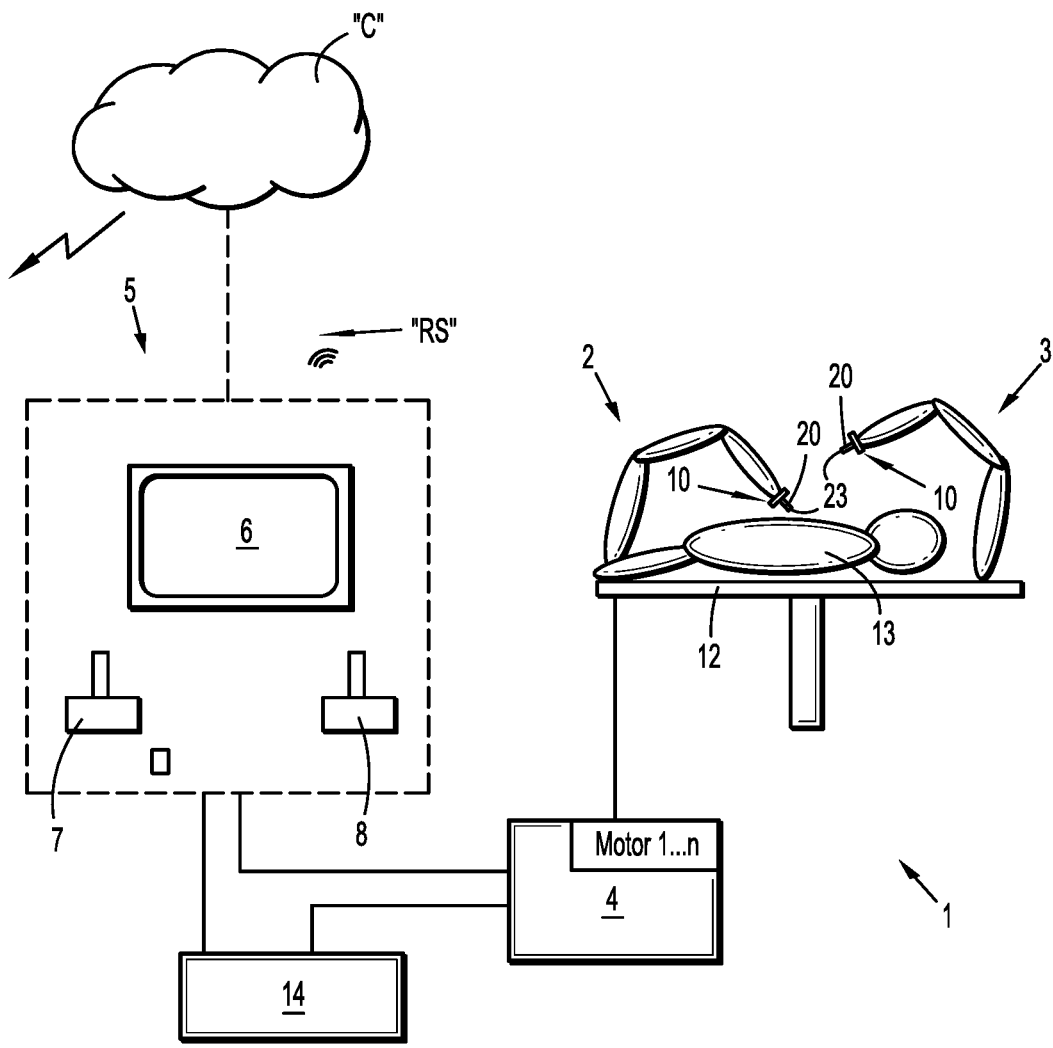
FIG. 1 is a schematic illustration of a surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

Referring initially to FIG. 1, a surgical system, such as, for example, a robotic surgical system is shown generally as surgical system 1 and generally includes a plurality of robotic arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Figure 2:
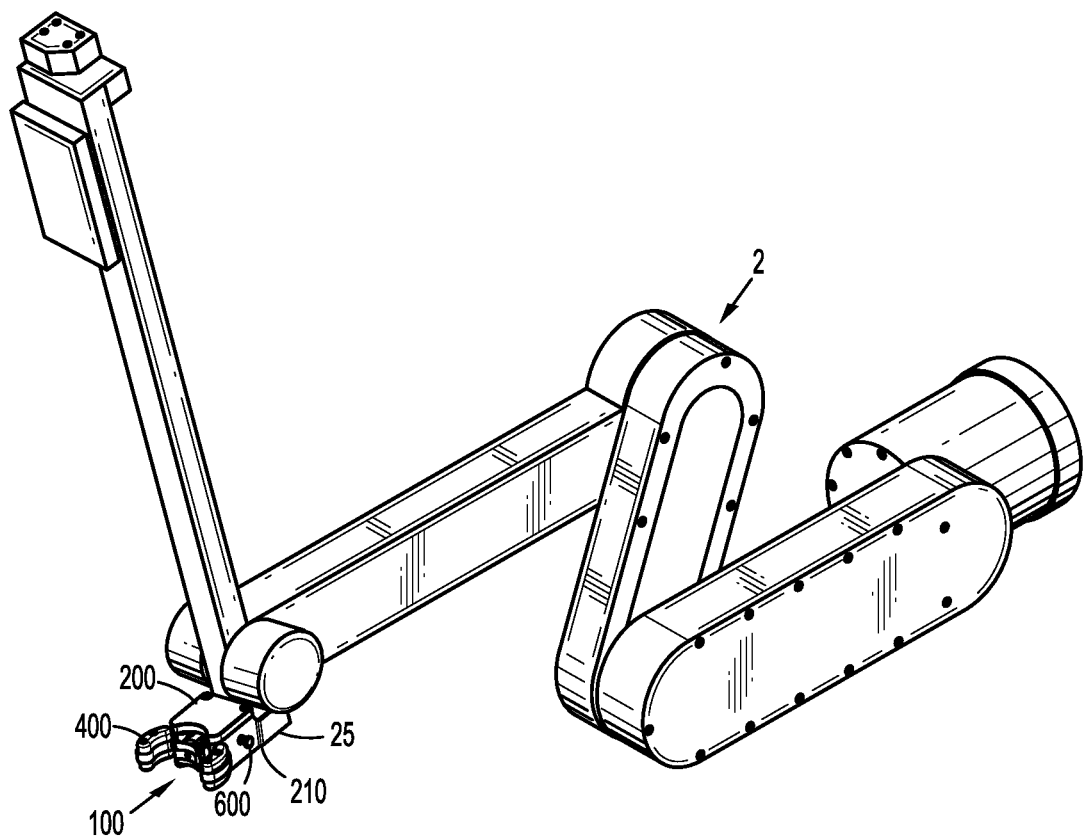
FIG. 2 is a perspective view of a robotic arm of the surgical system of FIG. 1.

Each of the robotic arms 2, 3 is composed of a plurality of members, which are connected through joints. System 1 also includes a surgical assembly 10 connected to a distal end of each of robotic arms 2, 3. A surgical instrument 20 supporting an end effector 23 may be attached to surgical assembly 10. As illustrated in FIG. 2, and in accordance with any one of several embodiments disclosed herein, the distal end of each robotic arm 2, 3 may further support a surgical mounting device 100, configured to releasably secure an access device therein, as will be described in greater detail below. Surgical mounting device 100 may be configured to receive any number of access tools or instruments, such as, for example, a trocar, surgical port, cannula or retractor.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their surgical assemblies 10 and/or surgical instruments 20 execute a desired movement according to a movement defined by means of manual input devices 7, 8. Control device 4 may also be set up in such a way that it regulates movement of robotic arms 2, 3 and/or of the drives.

Surgical system 1 is configured for use on a patient 13 lying on a patient table 12 to be treated in a minimally invasive manner by means of an end effector. Surgical system 1 may also include more than two robotic arms 2, 3, the additional robotic arms likewise being connected to control device 4 and being telemanipulatable by means of operating console 5. One or more additional surgical assemblies 10 and/or surgical instruments 20 may also be attached to the additional robotic arm.

Control device 4 may control a plurality of motors (Motor 1 . . . n) with each motor configured to drive a pushing or a pulling of one or more cables such as cables (not shown) coupled to end effector 23 of surgical instrument 20. In use, as these cables are pushed and/or pulled, the one or more cables effect operation and/or movement of end effector 23 of surgical instrument 20. It is contemplated that control device 4 coordinates the activation of the various motors (Motor 1 . . . n) to coordinate a pushing or a pulling motion of one or more cables in order to coordinate an operation and/or movement of one or more end effectors 23. In embodiments, each motor can be configured to actuate a drive rod or a lever arm to effect operation and/or movement of end effectors 23 in addition to, or instead of one or more cables.

Control device 4 can include any suitable logic control circuit adapted to perform calculations and/or operate according to a set of instructions. Control device 4 can be configured to communicate with a remote system "RS," either via a wireless (e.g., Wi-Fi, Bluetooth, LTE, etc.) and/or wired connection. Remote system "RS" can include data, instructions and/or information related to the various components, algorithms, and/or operations of work station 1. Remote system "RS" can include any suitable electronic service, database, platform, cloud "C" (see FIG. 1), or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of work station 1, such as through a driver circuit. Control device 4 can be configured to receive input signals and/or generate output signals to control one or more of the various components (e.g., one or more motors) of work station 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS."

Reference may be made to U.S. patent application Ser. No. 13/288,614, filed on Nov. 3, 2011, now U.S. Pat. No. 8,828,023, the entire content of which is incorporated herein by reference, for a detailed discussion of the construction and operation of surgical system 1.

Figure 3:
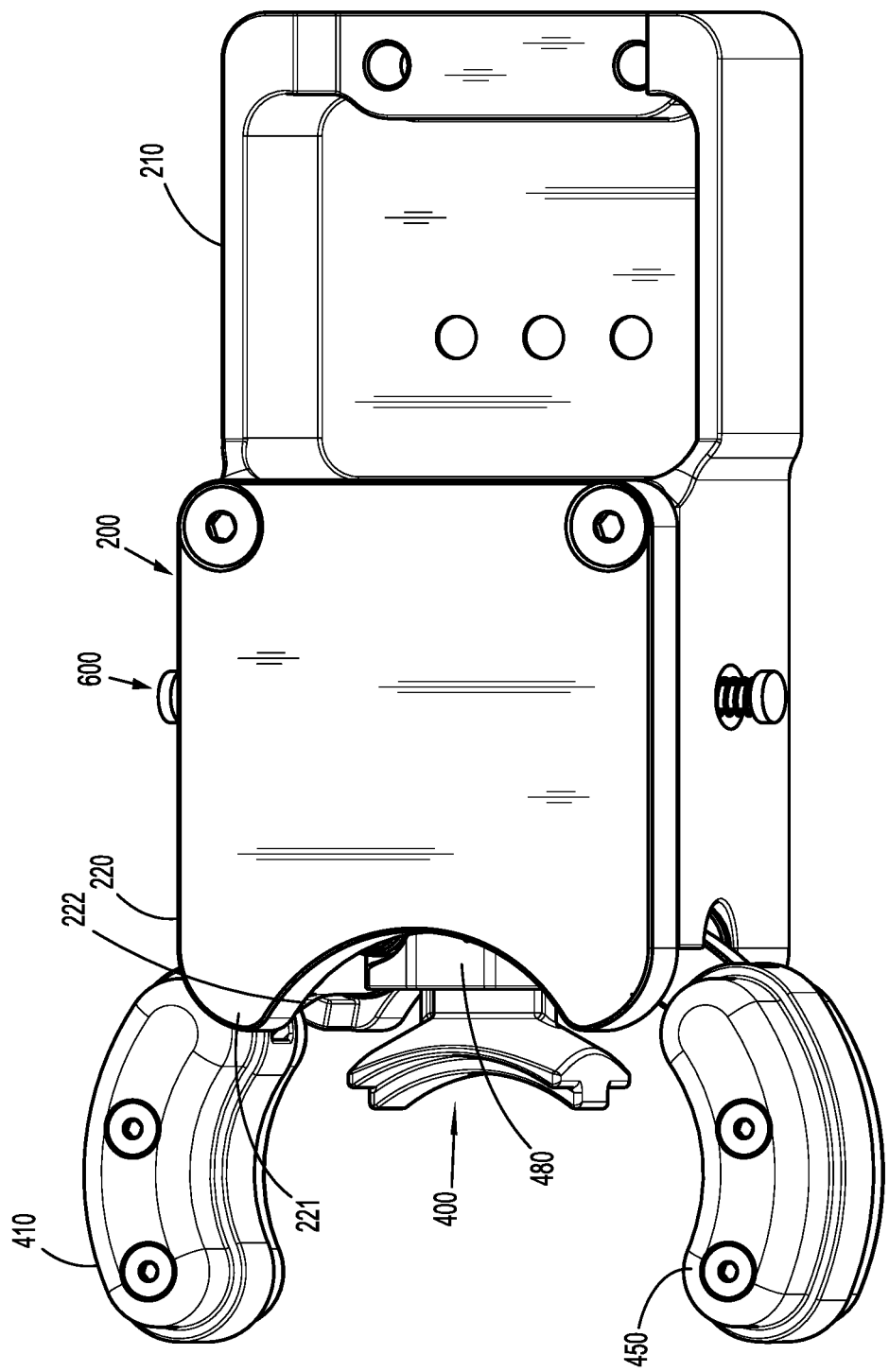
FIG. 3 is a front perspective view of a mounting device of the robotic arm of FIG. 2.
Figure 4:
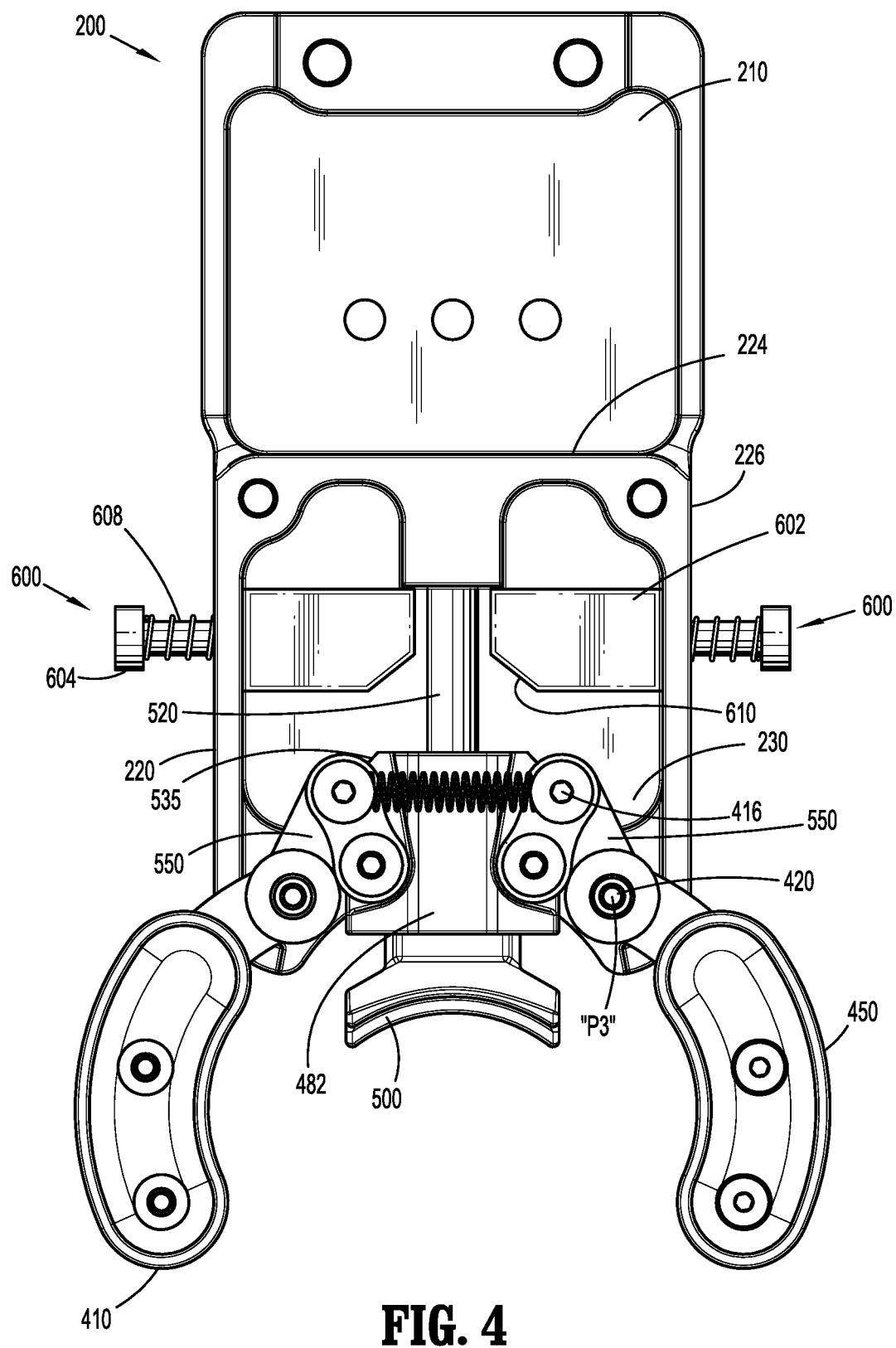
FIG. 4 is a top plan view of the mounting device of FIG. 3, with a cover removed therefrom.
Figure 7A:
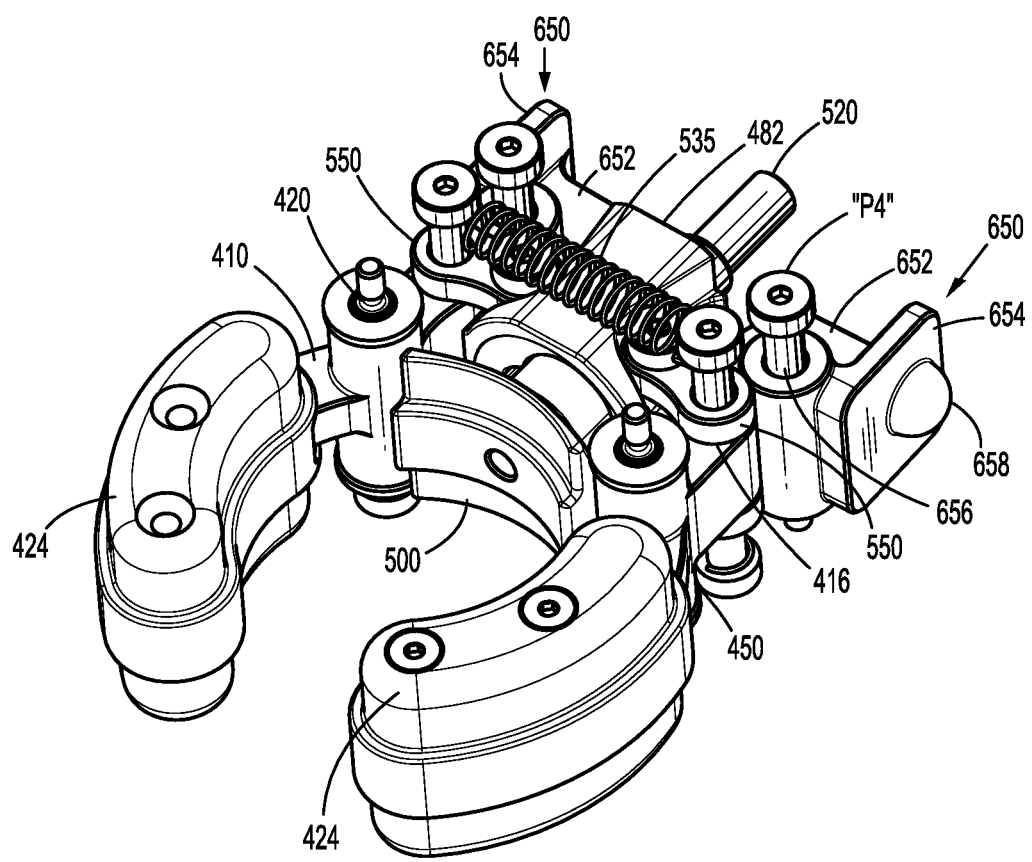
FIG. 7A is a rear perspective view of another embodiment of the clamping assembly of FIG. 4.
Figure 7B:
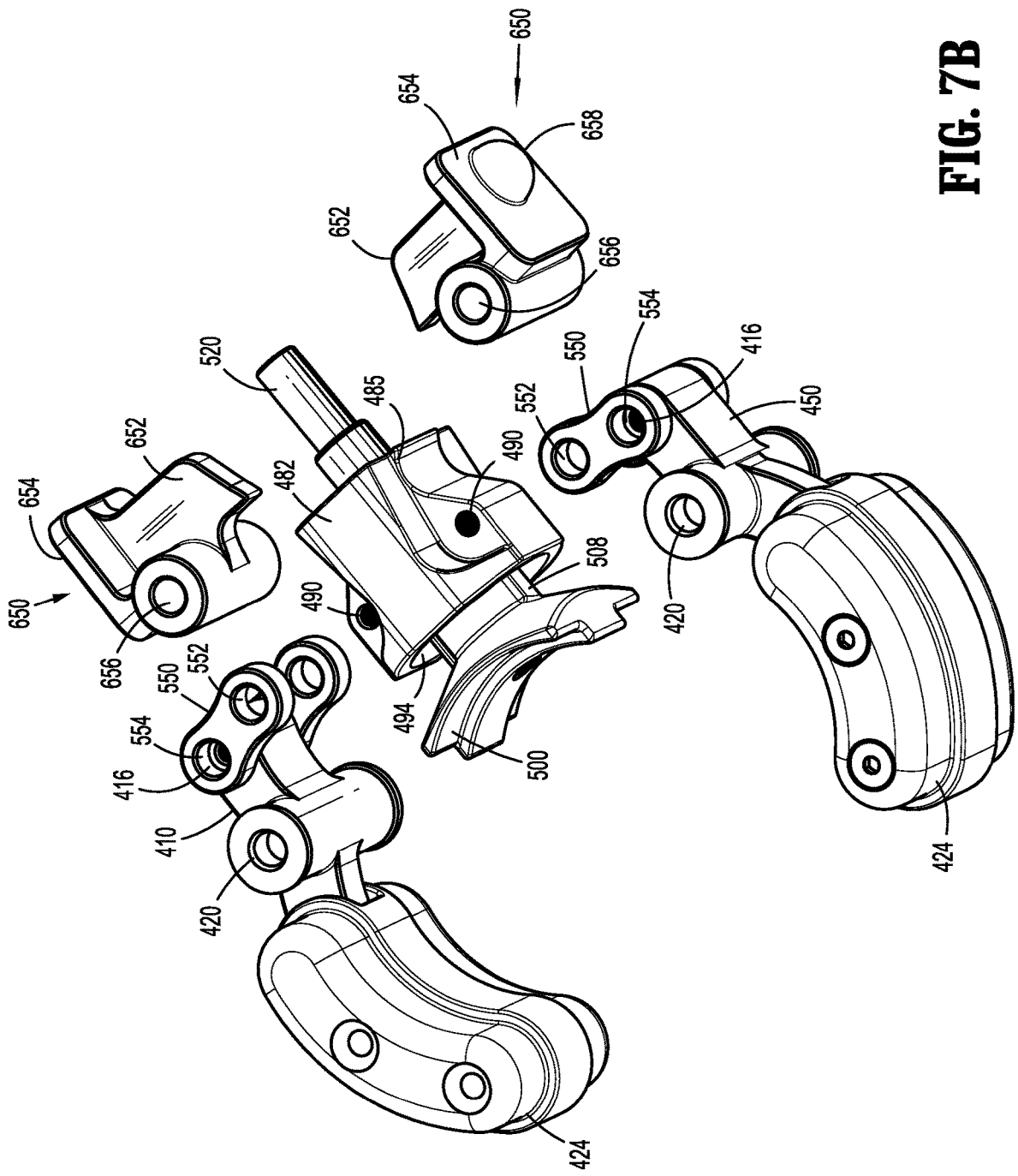
FIG. 7B is a perspective view, with parts separated, of the clamping assembly of FIG. 7A.
Figure 8A:
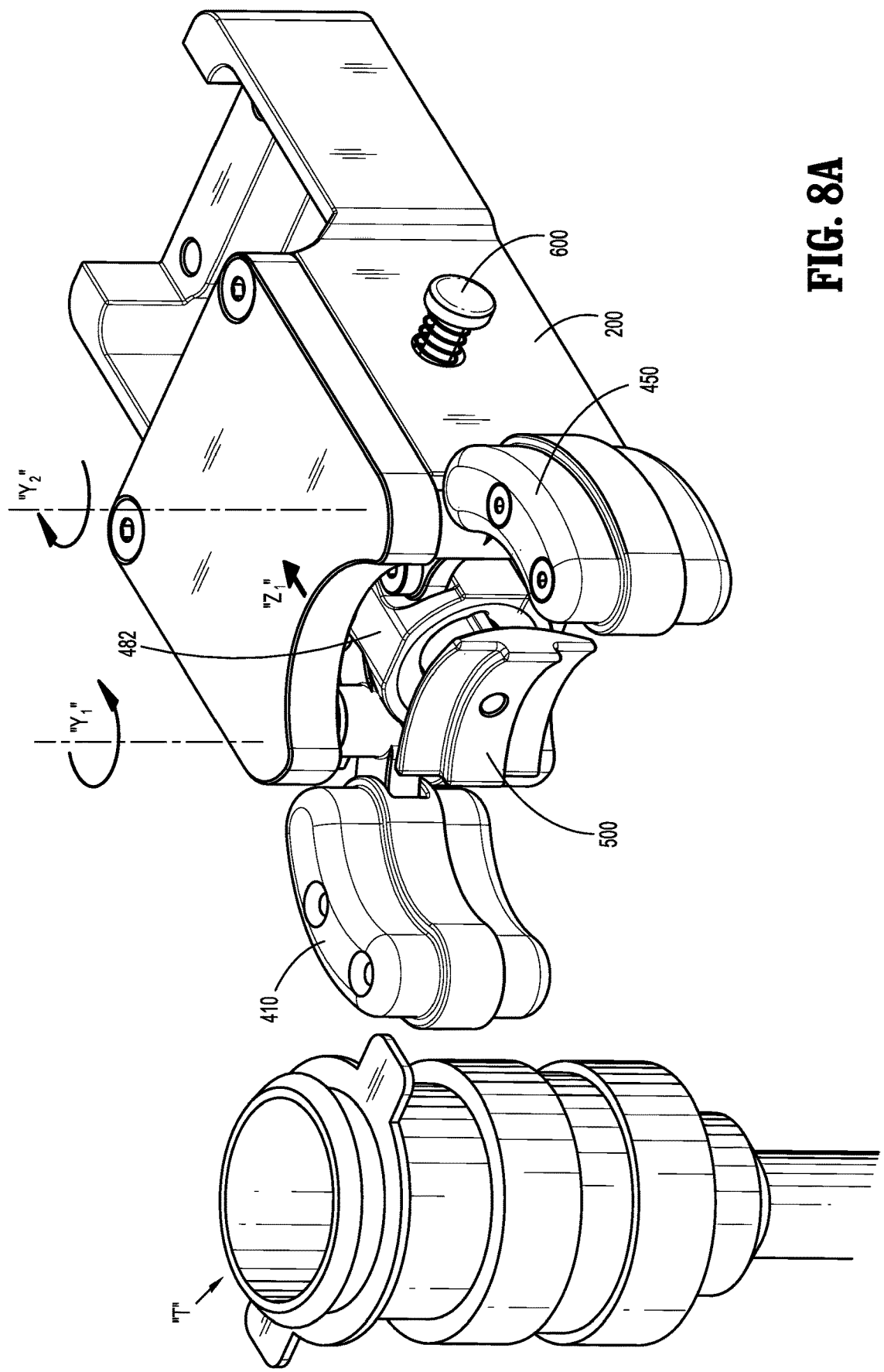
FIG. 8A is a perspective view of the mounting device of FIG. 4, with the clamping assembly in an unlocked configuration, for receipt of an access device therein.
Figure 8B:
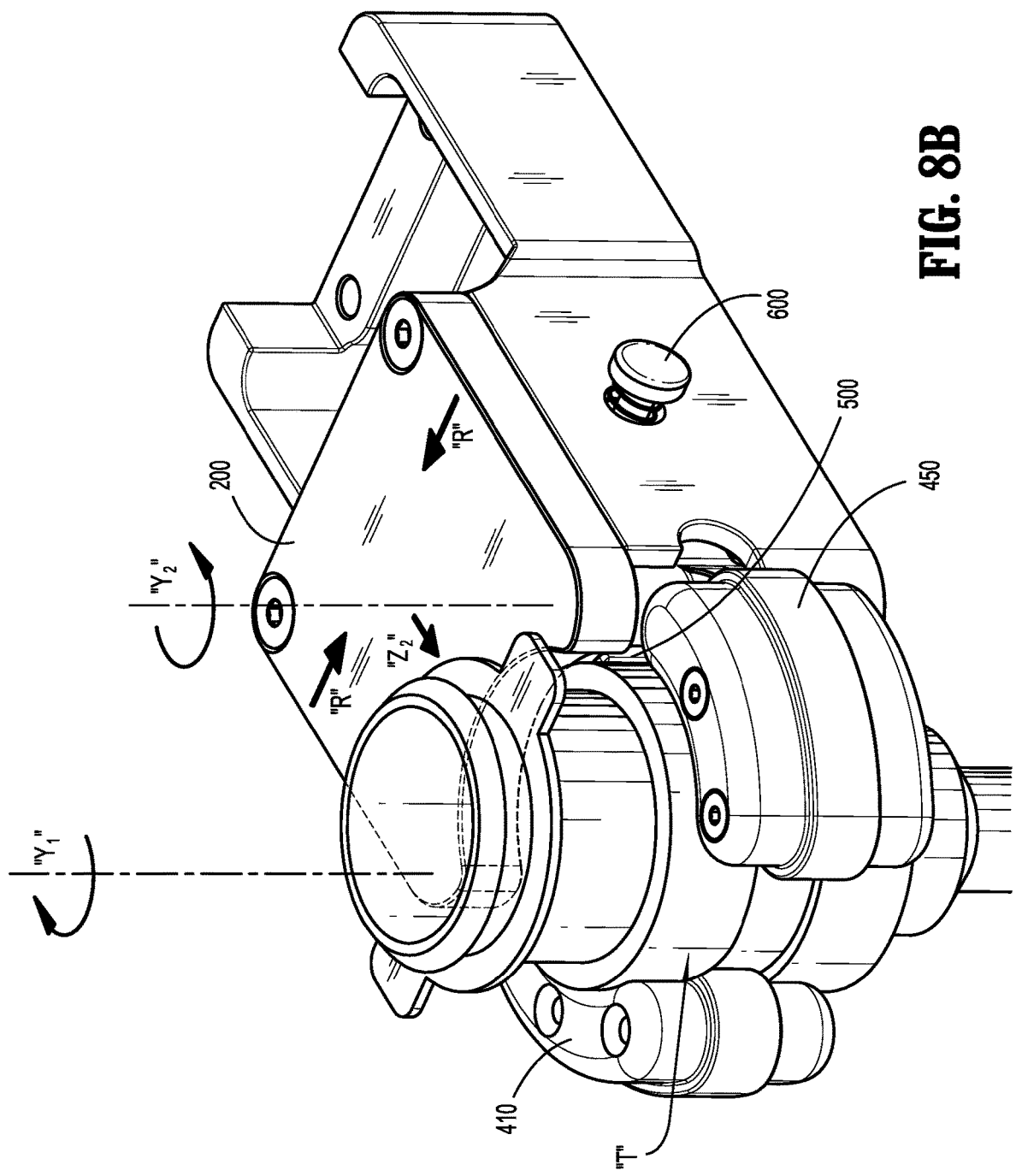
FIG. 8B is a perspective view of the mounting device of FIG. 4, with the clamping assembly in a locked configuration, and with the access device secured therein.

As illustrated in FIGS. 2-4, surgical mounting device 100 is coupled to robotic arm 2 (for example), and includes a housing 200 which supports a clamping assembly 400 and a release mechanism 600, or release mechanisms 650 (FIGS. 7A and 7B). Surgical mounting device 100 is configured to provide an easy and efficient structure to selectively secure a variety of access tools therein, thereby mounting an access device to the robotic arm. Surgical mounting device 100 further enables an access device docked therein to rotate 360 while maintaining secure fixation therein. While it is envisioned that surgical mounting device 100 may be adapted to receive a variety of access device therein, an access device in the form of a trocar "T" (as seen in FIGS. 8A and 8B) will be discussed in detail herein. Through a transition between an open configuration and a closed configuration of clamping assembly 400, trocar "T" may be releasably secured within surgical mounting device 100 such that trocar "T" is secured to robotic arm 2, as discussed below.

Housing 200 may be made of any suitable material (e.g., stainless steel) such that the clamping assembly 400 and the release mechanism 600 may be securely supported thereon. It is envisioned that housing 200 may be monolithically formed, or alternatively may have a multi-piece construction. Housing 200 includes a proximal portion 210 adapted to couple to a distal end 25 of the surgical arm 2 (FIG. 2), and a distal portion 220 adapted to support clamping assembly 400 and release mechanism 600. The distal portion 220 of housing 200 defines a cavity 230, such that clamping assembly 400 and release mechanism 600 are partially disposed therein, as discussed below.

A distal surface 221 of distal portion 220 of housing 200 may further define a receiving recess 222 which is configured to complement an exterior profile of an access device (FIGS. 8A and 8B), such that the access device may be positioned in near abutment to, or approximated within the distal surface 221 of housing 200. It is envisioned that the receiving recess 222 may be adapted to complement a variety of access tools enabling surgical mounting device 100 to secure a variety of access tools to robotic arm 2. As illustrated herein, receiving recess 222 defines an arcuate profile which complements the external profile of trocar "T" (FIGS. 8A and 8B), such that trocar "T" may be placed in near abutment to, and/or approximated with distal surface 221 of housing 220.

Clamping assembly 400 extends distally from cavity 230 of housing 200 and is transitionable between an open configuration and a closed configuration. With trocar "T" in near abutment to, or approximated with clamping assembly 400, clamping assembly 400 can be transitioned into the closed configuration such that trocar "T" is releasably secured therein.

Figure 5:
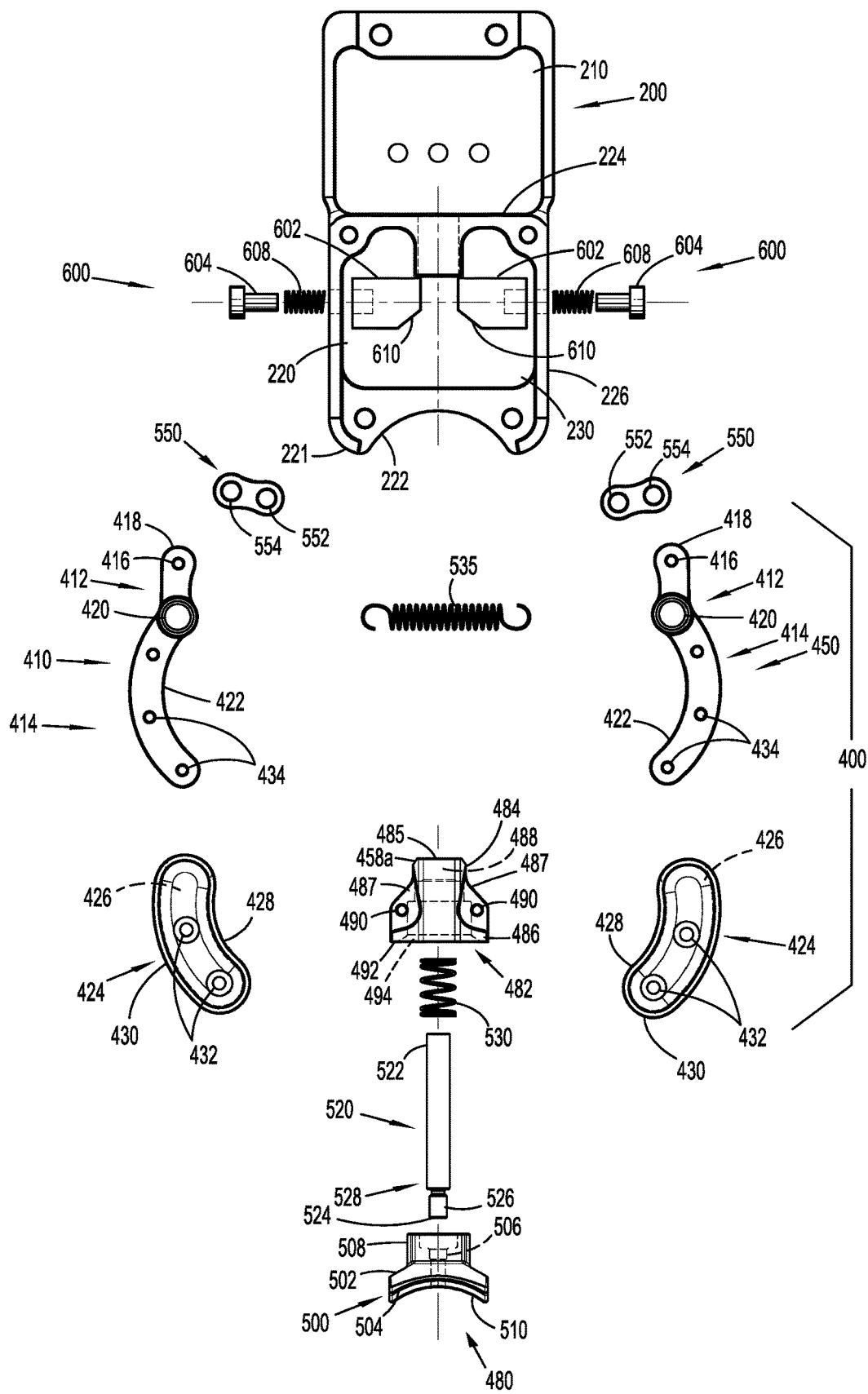
FIG. 5 is a plane view, with parts separated, of the mounting device of FIG. 4.

With additional reference to FIG. 5, clamping assembly 400 includes a first arm 410 positioned opposite a second arm 450, and a plunger assembly 480 positioned therebetween. It should be appreciated that first arm 410 is substantially similar to second arm 450, and thus, in the interest of brevity, the discussion of second arm 450 will be omitted and first and second arms 410, 450 will be described herein with like reference numerals.

First arm 410 includes a proximal portion 412 disposed in the cavity 230 of housing 200 and a distal portion 414 extending distally therefrom. First arm 410 defines a first through-hole 416 at a proximal end 418 thereof and a second through-hole 420 distal to the proximal end 418 thereof. First arm 410 may further define a receiving surface 422, distal of second through-hole 420, disposed on an inner facing surface with respect to second arm 450. It is envisioned that receiving surface 422 is configured to complement an exterior profile of an access device (FIGS. 8A and 8B) in a similar fashion as receiving recess 222 of housing 200 discussed above. In this manner, receiving surface 422 of first arm 410, and thus clamping assembly 400 of surgical mounting device 100, may accommodate a variety of access tools enabling a variety of access tools to be releasably secured to robotic arm 2. As illustrated herein, receiving surface 422 of first arm 410 provides an arcuate profile which complements the external profile of trocar "T" (FIGS. 8A and 8B), such that trocar "T" may be received therein.

First arm 410 may further include a cover or sleeve 424 configured to slidably engage with the distal portion 414 thereof, such that the distal portion 414 is disposed within a channel 426 (shown in phantom) of cover 424. It is envisioned that channel 426 is configured to accommodate a contour of the distal portion 414 of first arm 410, and further, that an exterior contour 428 of cover 424 is configured to mirror the receiving surface 422 of first arm 410. Cover 424 may be secured to first arm 410 by any means known in the art, such as, for example, glue, screws, pins, frictional engagement, etc. As illustrated herein, cover 424 is secured to first arm 410 via a plurality of screws (not shown) which extend through through-holes 432 of cover 424 and a corresponding number of through-holes 434 of first arm 410.

Cover 424 may further include a protruding ridge, rib, or shoulder 430 disposed along the exterior contour 428 configured to engage a complementary channel, race, or surface of an access device or trocar "T", as illustrated in FIGS. 8A and 8B. It is envisioned that the protruding ridge 430 provides greater ease when positioning, and better fixation when mounting, an access device within the first and second arms 410, 450 of clamping assembly 400.

Figure 6A:
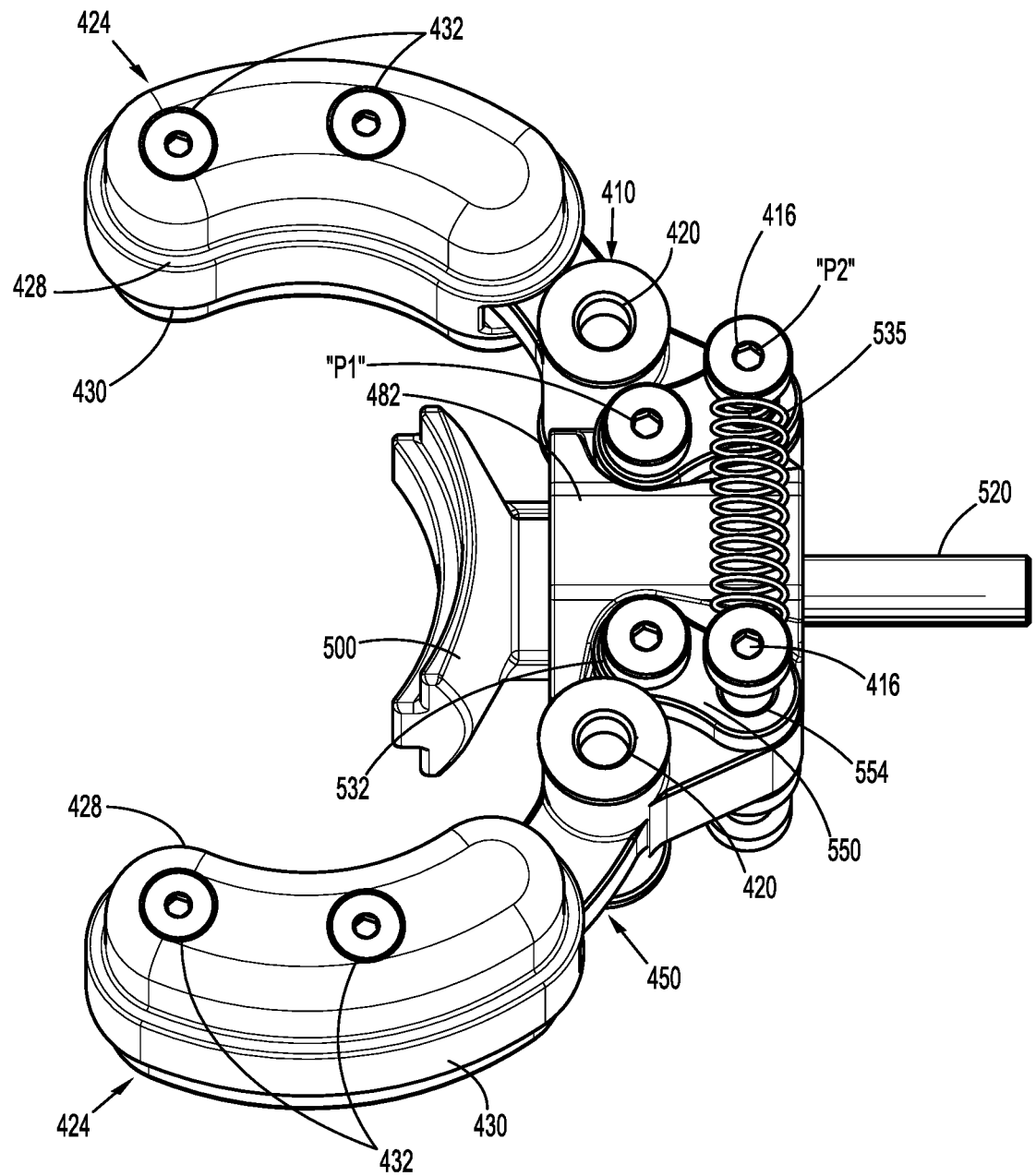
FIG. 6A is a perspective view of an embodiment of a clamping assembly of the mounting device of FIG. 4.
Figure 6B:
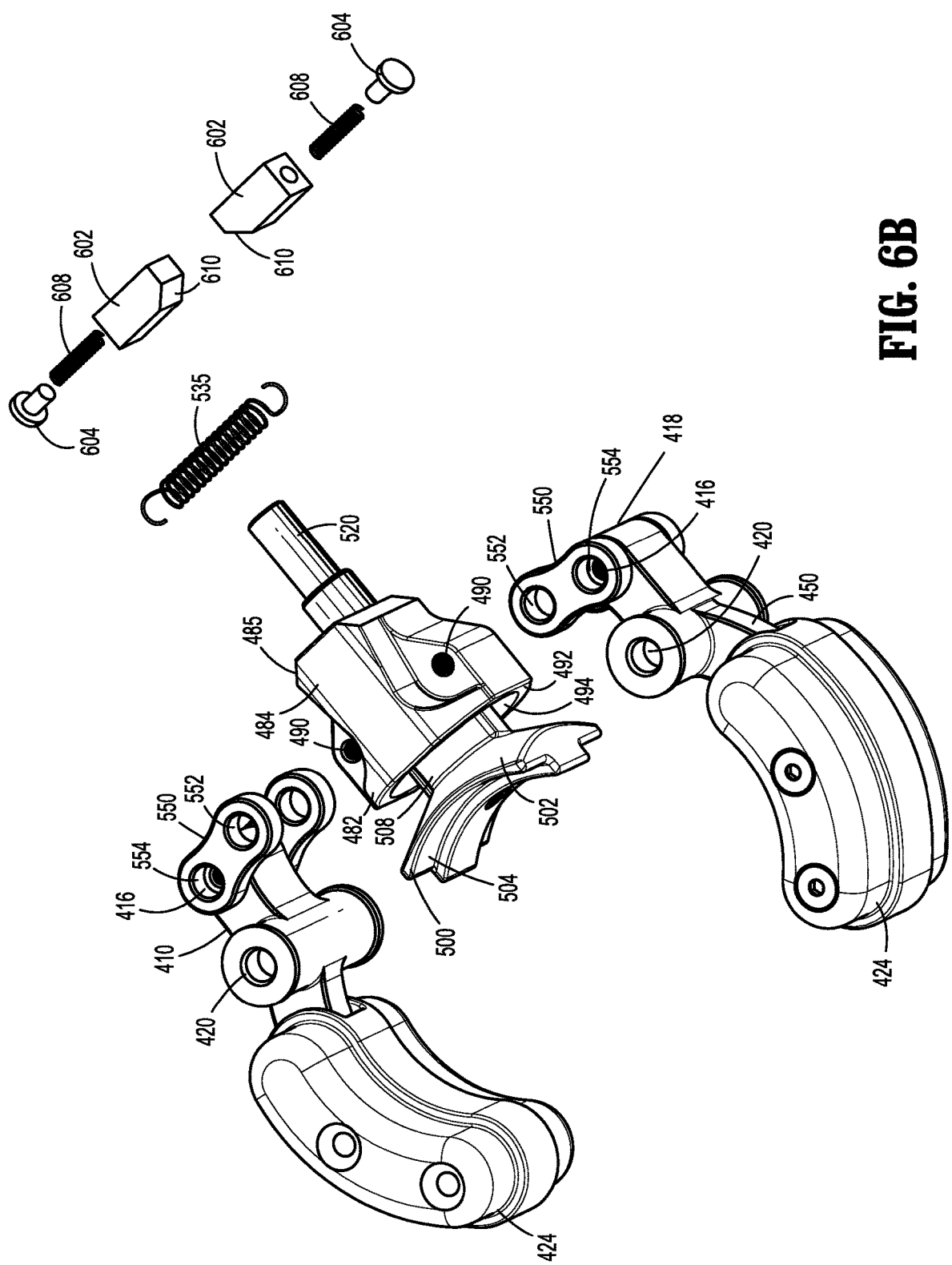
FIG. 6B is a perspective view, with parts separated, of the clamping assembly of FIG. 6A.

Clamping assembly 400 includes at least one link 550 pivotably interconnecting each of the first and second arms 410, 450, in a similar fashion, to drive member 482. Accordingly, only a detailed description of link 550 will be provided herein with reference to first arm 410. Link 550 defines a first through-hole 552 and a second through-hole 554, such that a cylindrical body, such as, for example, a pin or screw (not shown), may pass therethrough. A first pin "P1" (FIG. 6A) is disposed within the first through-hole 552 of link 550 and within through-hole 490 of drive member 482, such that link 550 is coupled to drive member 482. A second pin "P2" (FIG. 6A) is disposed within the second through-hole 554 of link 550 and within the first through-hole 416 of first arm 410, thereby coupling first arm 410 to link 450 and thus drive member 482. A third pin "P3" (FIG. 4) is disposed within second through-hole 420 of first arm 410 and may be secured to housing 200 at a position proximal to the distal surface 221 of housing 200. It should be appreciated that the first arm 410 second arms 450 of the clamping assembly 400 pivot about second through-hole 420 and the third pin "P3".

Clamping assembly 400 may further include at least one biasing member 535 coupled between the respective second pin "P2" disposed within the first through-hole 416 of the first arm 410 and within the first through-hole 416 of second arm 450. Biasing member 535 provides a biasing force between first and second arms 410, 450, such that first and second arms 410, 450 are pivotably biased into an open position, as discussed below. In an embodiment, a first biasing member 535 is coupled at a first end of second pin "P2", and a second biasing member 535 is coupled at an opposite second end of second pin "P2", such that two biasing members 535 are coupled between the first and second arms 410, 450.

With continued reference to FIGS. 4 and 5, plunger assembly 480 of clamping assembly 400 includes a drive member 482 slidably supported in cavity 230 of the housing 200, and coupled to a middle segment 500, positioned distal to the housing 200 between first and second arms 410, 450. Drive member 482 includes a proximal portion 484, a distal portion 486, and defines a longitudinal through-hole 488 (shown in phantom) extending therethrough. It is envisioned that distal portion 486 may narrow at the transition to the proximal portion 484, so as to define a notch or shoulder 487 therebetween. A proximal end 485 of the proximal portion 484 may further define a surface 485a to complement and engage with release mechanism 600. For example, surface 485a may be a chamfered or planar surface disposed on either side of the longitudinal through-hole 488, as discussed below.

Distal portion 486 of drive member 482 further defines a pair of through-holes 490 extending transverse to, and on opposing sides of, the longitudinal through-hole 488. A distal facing surface 492 of the distal portion 486 further includes a conical recess 494 (shown in phantom), such that a diameter of the longitudinal through-hole 488 increases as it approaches the distal facing surface 492 thereof.

Middle segment 500 of plunger assembly 480 of clamping assembly 400 includes a proximal surface 502, a distal surface 504, and defines a through-hole 506 (shown in phantom). Middle segment 500 may further include a circular base portion 508 extending proximally from the proximal surface 502, with through-hole 506 extending therein. It is envisioned that conical recess 494 of drive member 482 is complementary to the circular base portion 508, such that the circular base 508 may be received therein. Distal surface 504 of middle segment 500 is configured to complement an exterior profile of an access device (FIGS. 8A and 8B) in a similar fashion as receiving surface 422 of first arm 420 and receiving recess 222 of housing 200, discussed above, such that distal surface 504, and thus clamping assembly 400 of surgical mounting device 100 may accommodate a variety of access devices. As illustrated herein, distal surface 504 of middle segment 500 provides an arcuate profile which complements the external profile of trocar "T" (FIGS. 8A and 8B), such that trocar "T" may be approximated thereto. Distal surface 504 of middle segment 500 may further include a protruding ridge, rib, or shoulder 510 disposed transverse to the longitudinal through-hole 506 configured to engage a complementary channel, race, or surface of an access device or trocar "T", as illustrated in FIGS. 8A and 8B. Protruding ridge 510 provides greater ease when positioning, and better fixation when mounting, an access device to clamping assembly 400.

Drive member 482 of plunger assembly 580 of clamping assembly 400 may be coupled to middle segment 500 by any means known in the art, such as, for example, a bar or linkage. With drive member 482 coupled to middle segment 500, any movement by one causes a corresponding movement to the other, as discussed below. In an embodiment, drive member 482 and middle segment 500 are coupled to one another via a coupling bar 520. Coupling bar 520 is slidably supported at a proximal end 522 to a distal wall 224 of housing 200 that partially defines cavity 230 thereof, passes through the longitudinal through-hole 488 of the drive member 482, and supports, at a distal end 524 thereof, the middle segment 500 via through-hole 506. It is envisioned that coupling bar 520 may further include a threaded post or stem 526 extending distally from the distal end 524, such that coupling bar 520 can threadably engage with the through-hole 506 of the middle segment 500.

Plunger assembly 480 may further include another biasing member 530 disposed between the distal surface 504, or circular base portion 508, of the middle segment 500 and the conical recess 594 of drive member 482. Biasing member 530 may be disposed about a distal portion 528 of coupling bar 520 such that coupling bar 520 provides radial support to biasing member 530 when undergoing compressive forces. It is envisioned that biasing member 530 biases the middle segment 500 distally, with respect to drive member 482, such that middle segment 500 is biased towards a spaced apart position with respect to drive member 482.

With reference to FIGS. 4, 5, 8A and 8B, actuation of clamping assembly 400 will be described. As referenced above, clamping assembly 400 is transitionable between an open, or unlocked, configuration (FIG. 8A) and a closed, locked, configuration (FIG. 8B). It should be appreciated that the pivoting of first and second arms 410, 450 and the translation of drive member 482 and middle segment 500 correspond to the transition of the clamping assembly 400 between the open and closed configurations. First and second arms 410, 450 are pivotable about through-hole 420, which corresponds to axis "$Y_1$" and "$Y_2$" respectively, between a spaced apart position (FIG. 8A) and an approximated position (FIG. 8B) relative to one another. Drive member 482 and middle segment 500 coupled therewith are translatable between a distal position (FIG. 8A) and a proximal position (FIG. 8B) with respect to housing 200, as indicated by arrows "$Z_1$" and "$Z_2$". In the open configuration of clamping assembly 400, first and second arms 410, 450 are in the spaced apart position and drive member 482 and middle segment 500 are in the distal position (FIG. 8A). In the closed configuration of clamping assembly 400, first and second arms 410, 450 are in the approximated position and drive member 482 and middle segment 500 are in the proximal position (FIG. 8B).

It should be appreciated that actuation of first arm 410, second arm 450, drive member 482, and middle segment 500 are interconnected. Thus, clamping assembly 400 can be transitioned from the open configuration to the closed configuration by manually pivoting first and second arms 410, 450, about axis "$Y_1$" and "$Y_2$" respectively, from the spaced apart position to the approximated position, which in turn translates the drive member 482, and middle segment 500 coupled therewith, in the direction of arrow "$Z_1$" from the distal position to the proximal position. Clamping assembly 400 can alternatively be transitioned from the open configuration to the closed configuration by manually translating the middle segment 500, and drive member 482 coupled therewith, in the direction of arrow "$Z_1$" from the distal position to the proximal position, which in turn pivots the first and second arms 410, 450, about axis "$Y_1$" and "$Y_2$" respectively, from the spaced apart position to the approximated position. As discussed above, biasing member 535 acts to bias first and second arms 410, 450 into the open position, which is overcome as the clamping assembly 400 transitions into the closed configuration.

It is envisioned that drive member 482 may be operably coupled with a motor, servo, electro-controller, or any other means known in the art to achieve automated translation of drive member 482 in the direction of arrow "$Z_1$". In such an embodiment, a motor (not shown) is coupled to drive member 482 to effectuate the translation of drive member 482 from the distal position to the proximal position. As drive member 482 is translated into the proximal position, the middle segment 500 coupled therewith is translated into the proximal position and first and second arms 410, 450 are pivoted into the approximated position, thus transitioning the clamping assembly 400 into the closed configuration. A controller (not shown) may be included on an external surface of housing 200, disposed on robotic arm 2, or located at a peripheral location such that the motor can be activated remotely. It should be appreciated that the motor can similarly translate drive member 482 into the distal position in the direction of arrow "$Z_2$" (FIG. 8B). As the drive member 482 translates distally middle segment 500 coupled therewith is translated into the distal position and first and second arms 410, 450 are pivoted into the spaced apart position, thus transitioning the clamping assembly 400 into the open configuration.

With further reference to FIGS. 4 and 5, at least one release mechanism 600 may be partially disposed in the cavity 230 of housing 200. Release mechanism 600 includes a contact or cam member 602 disposed in the cavity 230 and which is coupled to an actuation member or button 604. Cam member 602 includes a contact or cam surface 610 configured to complement a surface of the proximal end 485 of the drive member 482, such as, for example, a complementary chamfered surface. Actuation member 604 extends through housing 200 and may include an ergonomic feature thereon. It is envisioned that actuation member 604 may take the form of a push button (as illustrated in FIGS. 4 and 5) or any other suitable geometry such that a portion is disposed external to housing 200. In an embodiment, a biasing member 608 is disposed between actuation member 604 and cam member 602, and/or housing 200 and release mechanism 600, such that cam member 602 is biased to an initial position, as discussed below. Further, cam member 602 and actuation member 604 may be monolithically formed.

With reference to FIGS. 8A and 8B, release mechanism 600 is actuatable between an initial position (FIG. 8A) and a release position (FIG. 8B). In the initial position the cam surface 610 of release mechanism 600 is spaced away from the proximal end 485 of the drive member 482. In the release position, release mechanism 600 is actuated in the direction of arrow "R" and the contact surface 610 of release mechanism 600 comes into abutment with the proximal end 485 of the drive member 482, such that the drive member 482 is urged to translate into the distal position in the direction of "$Z_2$". As the drive member 482 translates to the distal position the middle segment 500 coupled therewith concurrently translates into the distal position and the first and second arms 410, 450 pivot about axis "$Y_1$" and "$Y_2$" respectively into the spaced apart position, thus transitioning clamping assembly 400 into the open configuration. With clamping assembly 400 in the open configuration, the access device previously secured therein can be removed from surgical mounting device 100.

With reference to FIGS. 7A and 7B, an alternate embodiment of release mechanism 600 is illustrated and referenced as release mechanism 650. Release mechanism 650 may be inset onto a side wall 226 partially defining cavity 230 of housing 200, and includes a hooked portion 652 extending into cavity 230 adapted to engage a surface of the proximal end 485 of drive member 482 in a release position, as discussed below, and an external surface 654 being flush with housing 200 in an initial position (not shown). Release mechanism 650 further defines a through-hole 656 such that release mechanism 650 is pivotable about through-hole 656 and a fourth pin "P4" (FIG. 7A) disposed therein between an initial position and a release position. It is envisioned that the external surface 654 may include an ergonomic feature 656 disposed thereon. In an embodiment, a biasing member (not shown) is coupled to release mechanism 650 such that release mechanism 650 is biased into the initial position. Further, hooked portion 652 and external surface 654 may be monolithically formed.

Release mechanism 650 is actuatable between an initial position and a release position (not shown). In the initial position, the external surface 654 of release mechanism 650 may be substantially flush with housing 220, and the hooked portion 652 is spaced away from the proximal end 485 of the drive member 482. In the release position, release mechanism 650 is pivoted about pin "P4", such that the hooked portion 652 comes into abutment with the proximal end 485 of the drive member 482. As release mechanism 650 continues to pivot, hooked portion 650 urges drive member 482 to translate into the distal position in the direction of "$Z_2$", concurrently causing the middle segment 500 coupled therewith to translate to the distal position and the first and second arms 410, 450 to pivot about "$Y_1$" and "$Y_2$", respectively, into the spaced apart position, thus transitioning clamping assembly 400 into the open configuration.

As discussed above, biasing member 535 acts to bias first and second arms 410, 450 into the open position, and is overcome as the clamping assembly 400 transitions into the closed configuration. During the transition of clamping assembly 400 from the closed configuration to the open configuration, biasing member 535 facilitates the transition by providing a pivotable threshold. As the drive member 482 begins to translate from the proximal position to the distal position, the first and second arms 410, 450 begin to pivot from the approximated position to the spaced apart position. Once first and second arms 410, 450 pivot past the threshold, biasing member 535 springs or biases first and second arms 410, 450 into the spaced apart position. As a result of first and second arms 410, 450 being biased to the spaced apart position by biasing member 535, drive member 482, and middle segment 500 coupled therewith, are concomitantly sprung into the distal position, thus clamping assembly is sprung into the open configuration.

It is further envisioned that surgical mounting device 100 may include a sensor (not shown) configured to detect if an access device is properly and completely mounted therein. The sensor may be disposed about surgical mounting device 100, such as, for example, in housing 200, between first and second arms 410, 450, or on middle segment 500. The sensor may take any form known in the art, such as, for example, a hall-effect sensor, contact/contactless sensor, or IR beam. It is envisioned that a sensor and/or receiver may be disposed on an access device, which may or may not, be configured to cooperatively communicate with a corresponding sensor and/or receiver disposed on surgical mounting device 100, such that proper and complete docking may be detected.

In operation, with housing 200 of surgical mounting device 100 secured to robotic arm 2 and clamping assembly 400 initially placed in the open configuration, an access device is placed between first and second arms 410, 450 and into abutment with middle segment 500. The clamping device 400 is then transitioned to the closed configuration by pivoting first and second arms 410, 450 to the approximated position, and/or depressing or pressing the access device against the middle segment 500. As a result of pivoting first and second arms 410, 450, or depressing middle segment 500, drive member 482 is concurrently translated to the proximal position. As drive member 482, and middle segment 500 coupled therewith, translate proximally, the at least one link 550 coupling each of the first and second arms 410, 450 thereto causes first and second arms 410, 450 to begin pivoting to the approximated position, such that the pivotable threshold created by biasing member 535 of clamping assembly 400 is overcome. It should be appreciated that with drive member 482 in the proximal most position, drive member 482 and link 550 inhibit and prevent first and second arms 410, 450 from pivoting into the spaced apart position.

More specifically, in the open configuration of clamping assembly 400, the proximal portion 412 of each first and second arm 410, 450 is disposed in the shoulder 487 defined between the proximal portion 484 and the distal portion 486 of drive member 482. Shoulder 487 thus provides a recess for the proximal portion 412 of each first and second arm 410, 450 to reside when first and second arms 410, 450 are in the spaced apart position, and the clamping assembly 400 is in the open configuration. As drive member 482 translates proximally, link 550 directs the proximal portion 412 of each first and second arm 410, 450 to pivot out of, and away from, shoulder 487 such that first and second arms 410, 450 pivot to the approximated position. With drive member 482 in the proximal most position, first and second arms 410, 450 are inhibited from pivoting to the open position via the positioning of the proximal portion 412 of each first and second arm 410, 450 with respect to the shoulder 487 of drive member 481. Thus, with drive member 482 translated into the proximal most position, middle segment 500 and first and second arms 410, 450 are locked into the proximal and approximated positions, respectively.

To release the access device from surgical mounting device 100, release mechanism 600, 650 is actuated, such that the drive member 482 is urged to translate to the distal position. As drive member 482 is translated distally, middle segment 500 is caused to translate distally and first and second arms 410, 450 are caused to pivot to the open position, thereby transitioning the clamping assembly into the open configuration, as discussed herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be affected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical mounting device, comprising:
   a housing;
   a clamping assembly supported in the housing and extending therefrom, the clamping assembly including:
   a plunger assembly disposed in mechanical cooperation with the housing and including a drive member and a middle segment, wherein the drive member and the middle segment are configured to translate between a proximal position and a distal position relative to the housing;
   a first arm and a second arm, a proximal portion of the first arm and a proximal portion of the second arm coupled to the drive member, the first arm being pivotable with respect to the housing between an open position and a closed position, wherein in the open position the first arm and the second arm are spaced apart relative to one another and in the closed position the first arm and the second arm are in an approximated position relative to one another;
   a first biasing member including a first portion coupled to the first arm and a second portion coupled to the second arm, the first biasing member biasing the first arm toward the open position; and
   a second biasing member including a first portion coupled to the middle segment and a second portion coupled to the drive member, the second biasing member biasing the middle segment towards the distal position,
   wherein the clamping assembly is transitionable between an unlocked configuration and a locked configuration, such that in the unlocked configuration the drive member and the middle segment are in the distal position and the first arm is in the open position, and in the locked configuration the drive member and the middle segment are in the proximal position and the first arm is in the closed position, and
   at least one release mechanism including:
   a contact surface;
   an articulation member in operative communication with the contact surface,
   wherein the at least one release mechanism is transitionable between an initial position and a release position, such that in the initial position the contact surface is spaced away from the drive member; and
   a third biasing member biasing the at least one release mechanism towards the initial position.

2. The surgical mounting device according to claim 1, wherein when the at least one release mechanism is in the release position, the contact surface engages a surface of the drive member.

3. The surgical mounting device according to claim 1, wherein the at least one release mechanism includes two release mechanisms disposed on opposite sides of the housing.

4. The surgical mounting device according to claim 1, wherein the second arm is pivotable with respect to the housing between an open position and a closed position.

5. The surgical mounting device according to claim 4, wherein each of the first arm and the second arm includes a pivot point such that pivoting the first arm and the second arm from the open position to the closed position translates the drive member and the middle segment from the distal position to the proximal position, thereby transitioning the clamping assembly towards the locked configuration.

6. The surgical mounting device according to claim 4, wherein translation of the middle segment from the proximal position to the distal position causes the drive member to translate distally and causes the first arm and the second arm to pivot from the open position to the closed position, thereby transitioning the clamping assembly towards the locked configuration.

7. The surgical mounting device according to claim 1, wherein the drive member is disposed between the first arm and the second arm.

8. The surgical mounting device according to claim 1, wherein the at least one release mechanism includes a hooked end configured to engage a surface of the drive member.

9. The surgical mounting device according to claim 1, wherein the at least one release mechanism includes a chamfered profile configured to engage a surface of the drive member.

10. A surgical mounting device, comprising:
a housing;
a clamping assembly supported in the housing and extending therefrom, the clamping assembly including:
a plunger assembly disposed in mechanical cooperation with the housing and including a drive member and a middle segment, wherein the drive member and the middle segment are configured to translate between a proximal position and a distal position relative to the housing;
a first arm and a second arm, a proximal portion of the first arm and a proximal portion of the second arm coupled to the drive member, the first arm being pivotable with respect to the housing between an open position and a closed position, wherein in the open position the first arm and the second arm are spaced apart relative to one another and in the closed position the first arm and the second arm are in an approximated position relative to one another;
a first biasing member including a first portion coupled to the first arm and a second portion coupled to the second arm, the first biasing member biasing the first arm toward the open position; and
a second biasing member including a first portion coupled to the middle segment and a second portion coupled to the drive member, the second biasing member biasing the middle segment towards the distal position,
wherein the clamping assembly is transitionable between an unlocked configuration and a locked configuration, such that in the unlocked configuration the drive member and the middle segment are in the distal position and the first arm is in the open position, and in the locked configuration the drive member and the middle segment are in the proximal position and the first arm is in the closed position;
a first release mechanism disposed on a first side of the housing and including a contact surface, and an articulation member in operative communication with the contact surface, wherein the first release mechanism is transitionable between an initial position and a release position, such that in the initial position the contact surface is spaced away from the drive member; and
a second release mechanism disposed on a second side of the housing, the second side of the housing being opposite from the first side of the housing, the second release mechanism including a contact surface, and an articulation member in operative communication with the contact surface, wherein the second release mechanism is transitionable between an initial position and a release position, such that in the initial position the contact surface is spaced away from the drive member.

11. The surgical mounting device according to claim 10, wherein when the first release mechanism is in the release position, the contact surface engages a surface of the drive member.

12. The surgical mounting device according to claim 10, wherein the second arm is pivotable with respect to the housing between an open position and a closed position.

13. The surgical mounting device according to claim 12, wherein each of the first arm and the second arm includes a pivot point such that pivoting the first arm and the second arm from the open position to the closed position translates the drive member and the middle segment from the distal position to the proximal position, thereby transitioning the clamping assembly towards the locked configuration.

14. The surgical mounting device according to claim 12, wherein translation of the middle segment from the proximal position to the distal position causes the drive member to translate distally and causes the first arm and the second arm to pivot from the open position to the closed position, thereby transitioning the clamping assembly towards the locked configuration.

15. The surgical mounting device according to claim 10, wherein the first release mechanism further includes a third biasing member biasing the first release mechanism towards the initial position.

16. The surgical mounting device according to claim 10, wherein the drive member is disposed between the first arm and the second arm.

17. The surgical mounting device according to claim 10, wherein the first release mechanism includes a hooked end configured to engage a surface of the drive member.

18. The surgical mounting device according to claim 10, wherein the first release mechanism includes a chamfered profile configured to engage a surface of the drive member.

* * * * *